United States Patent

Blach et al.

(10) Patent No.: US 6,352,548 B1
(45) Date of Patent: Mar. 5, 2002

(54) NASAL SUPPORT DEVICE FOR ANIMALS AND METHOD

(75) Inventors: Edward L. Blach, Roswell, NM (US); James R. Chiapetta, Eagan; Daniel E. Cohen, Eden Prairie, both of MN (US)

(73) Assignee: WinEase LLC, Eagan, MN (US)

( * ) Notice: Subject to any disclaimer, the term of this patent is extended or adjusted under 35 U.S.C. 154(b) by 0 days.

(21) Appl. No.: 09/379,425

(22) Filed: Aug. 23, 1999

(51) Int. Cl.$^7$ .............................................. A61M 29/00
(52) U.S. Cl. ................... 606/199; 128/200.24
(58) Field of Search ..................... 606/199, 204.45; 128/200.24

(56) References Cited

U.S. PATENT DOCUMENTS

| | | |
|---|---|---|
| 1,232,956 A | 7/1917 | Mooney |
| 3,691,140 A | 9/1972 | Silver |
| 4,614,183 A * | 9/1986 | McCracken et al. .......... 602/57 |
| 4,994,322 A | 2/1991 | Delgado et al. |
| 5,266,402 A | 11/1993 | Delgato et al. |
| 5,476,091 A | 12/1995 | Johnson |
| 5,502,108 A | 3/1996 | Silver et al. |
| 5,533,499 A | 7/1996 | Johnson |
| 5,533,503 A | 7/1996 | Doubek et al. |
| 5,546,929 A | 8/1996 | Muchin |
| 5,549,103 A | 8/1996 | Johnson |
| 5,553,605 A | 9/1996 | Muchin |
| RE35,408 E | 12/1996 | Petruson |
| 5,611,333 A | 3/1997 | Johnson |
| 5,653,224 A | 8/1997 | Johnson |
| 5,669,377 A | 9/1997 | Fenn |
| 5,706,800 A | 1/1998 | Cronk et al. |
| 5,718,224 A | 2/1998 | Muchin |
| 5,719,247 A | 2/1998 | Delgado et al. |
| 5,755,232 A | 5/1998 | Kalt |
| 5,817,039 A | 10/1998 | Raunig |
| 5,890,486 A | 4/1999 | Mitra et al. |
| 5,913,873 A | 6/1999 | Blach et al. |
| 5,947,119 A | 9/1999 | Reznick |
| 5,976,173 A | 11/1999 | Berke |
| 6,017,357 A * | 1/2000 | Blach et al. .......... 606/204.45 |
| 6,033,422 A * | 3/2000 | Blach et al. ................ 606/199 |
| 6,065,470 A * | 5/2000 | Van Cromvoirt et al. ..... 128/200.24 |
| 6,098,616 A * | 8/2000 | Lundy, Jr. et al. ...... 128/200.24 |

FOREIGN PATENT DOCUMENTS

| | | |
|---|---|---|
| AU | A-65890/96 | 4/1998 |
| ES | 289561 | 10/1985 |
| GB | 768488 | 2/1957 |
| GB | 2313313 | 11/1997 |
| WO | WO 92/22340 | 12/1992 |
| WO | WO 94/23675 | 10/1994 |
| WO | WO 97/02793 | 1/1997 |
| WO | WO 98/12998 | 4/1998 |
| WO | WO 98/47451 | 10/1998 |

OTHER PUBLICATIONS

Amis et al., "Nasal vestibule wall elasticity: interactions with a nasal dilator strip," *J Appl Physiol* 86(5):1638–1643 (1999).

(List continued on next page.)

*Primary Examiner*—Glenn K. Dawson
(74) *Attorney, Agent, or Firm*—Merchant & Gould P.C.

(57) ABSTRACT

Devices and methods for facilitating air flow in the nasal passages of domestic animals. The devices include support devices for supporting unsupported tissues of the nasal passages which facilitate air flow during rest, physical exertion, respiratory ailment, etc. Components and methods to facilitate application of the support device to the nose of an animal are also disclosed.

13 Claims, 8 Drawing Sheets

OTHER PUBLICATIONS

Art et al., "Effect of exercise on the partitioning of equine respiratory resistance," *Equine Vet J* 20(4):268–273 (Jul. 1988).

Art et al., "Mechanics of breathing during strenuous exercise in thoroughbred horses," *Respir Physiol* 82:279–294 (1990).

Bruintjes et al., "A Functional Anatomic Study of the Relationship of the Nasal Cartilages and Muscles to the Nasal Valve Area," *The Laryngoscope*, 108:1025–1032 (Jul. 1998).

Declaration of James R. Chiapetta re: Kev's World Cartoon.

Di Somma et al., "Nasal dilator strips increase maximum inspiratory flow via nasal wall stabilization," *The Laryngoscope* 109:780–784 (May 1999).

Erickson, "Exercise induced pulmonary haemorrhage," Proceedings of the Fourth International Conference on Equine Exercise Physiology, (Jul. 11–16, 1994) in *Equine Vet J Suppl* 18:476–478 (1995).

Erickson et al., "Pulmonary artery, aortic and oesophageal pressure changes during high intensity treadmill exercise in the horse: a possible relation to exercise–induced pulmonary haemorrhage," *Equine Vet J. Suppl.* 9:47–52 (1990).

Erickson et al., "What Causes Racehorse Lungs to Bleed?," *The Quarter Racing J.*, 52–57 (May 1995).

Fedde et al., "Increase in blood viscosity in the sprinting horse: can it account for the high pulmonary arterial pressure?," *Equine Vet J.*, 30(4):329–334 (1998).

Foerner, "The Diagnosis and Correction fo False Nostril Noises," AAEP Proceedings, pp. 315–327 (1967).

Funkquist et al., "Studies on the intratracheal pressure in the exercising horse," *J. Vet. Med A*, 35:424–441 (1988).

Gillespie, "The role of respiratory system during exertion," *J S Afr Vet Assoc* 45(4):305–309 (1974).

Goetz et al., "Pressures in the right side of the heart and esophagus (pleura) in ponies during exercise before and after furosemide administration," *Am J Vet Res* 47(2):270–277 (Feb. 1986).

Guillette, "Use of Nasal Valve Stent with Anterior Rhynomanometry to Quantitate Nasal Valve Obstruction," *Ann. Otol. Rhinol. Laryngol*, 99:175–178 (1990).

Haight et al., "The Site and Function of the Nasal Valve," *Laryngescope* 93:49–55 (Jan. 1983).

Hinchcliff, "Effects of furosemide on athletic performance and exercise–induced pulmonary hemorrhage in horses," *J Am. Vet Med. Assoc.*, 215(5):630–635 (Sep. 1999).

Jackson et al., "Effects of airway obstruction on transmural pulmonary artery pressure in exercise horses," *Am J Vet Res* 58(8):897–903 (Aug. 1997).

Johnson et al., "Modelling exercise–induced pulmonary hemorrhage in racing thoroughbreds," *Frontiers Med Biol Eng* 4(4):271–289 (1992).

Jones et al., "The nasal valve: a physiological and clinical study," *J. of Laryngol. and Oto.*, 102:1089–1094 (Dec. 1988).

Lekeux et al. "The respiratory system: anatomy, physiology, and adaptations to exercise and training," *The Athletic Horse*, DR Hodgson and RJ Rose (eds), WB Saunders (1994).

Manohar, "Furosemide attenuates the exercise–induced increase in pulmonary artery wedge pressure in horses," *Am. J. Vet. Res.*, 54(6):952–958 (Jun. 1993).

Manohar, "Furosemide attenuates the exercise–induced rise in pulmonary capillary blood pressure in horses," *Equine Vet. J.*, 26(1):51–54 (1994).

McKane et al., "Equine bronchoalveolar lavage cytology: survey of Thoroughbred racehorses in training," *Aust. Vet. J.*, 70(11):401–404 (Nov. 1993).

Meyer et al., "Quantification of exercise–induced pulmonary haemorrhage with bronchoalveolar lavage," *Equine Vet. J.*, 30(4):284–288 (1998).

Olsen et al., "Influence of furosemide on hemodynamic responses during exercise in horses," *Am. J. Vet. Res.*, 53(5):742–747 (May 1992).

Robinson et al., "Pathophysiology of airway obstruction in horses: A Review," *J Am Vet Med Assoc*, 172(3):299–303 (Feb. 1978).

Roithmann et al., "Acoustic Rhinometric Assessment of the Nasal Valve," *American Journal of Rhinology*, 11(5):379–402 (1997).

Sinha et al., "Pleural pressure changes during exercise do not affect measurement of mean vascular pressures," *Equine Vet. J. Suppl.*, 18:95–98 (1995).

Whitwell et al., "Collection and evaluation of tracheobronchial washes in the horse," *Equine Vet. J.*, 16(6):499–508 (1984).

* cited by examiner

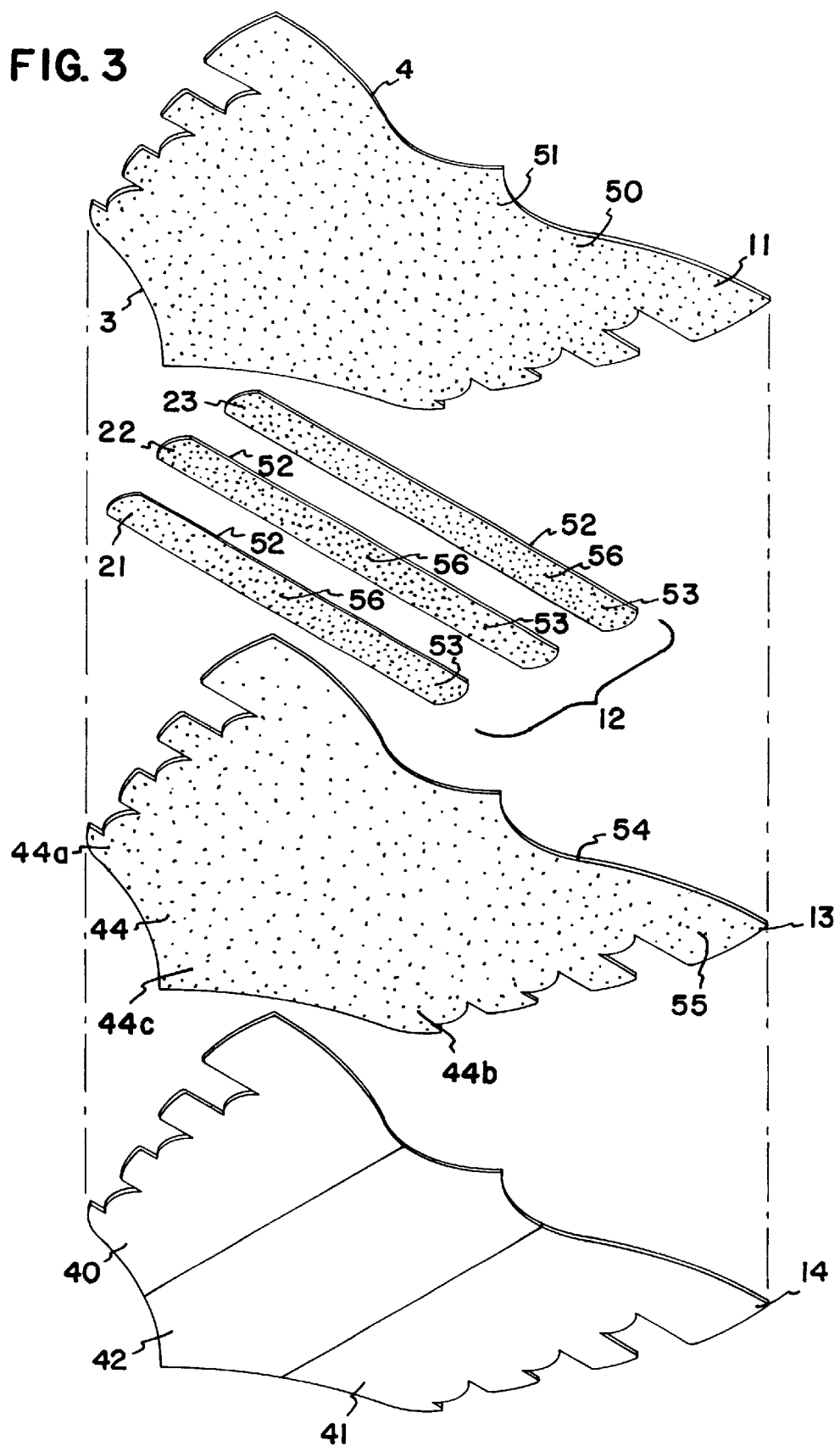

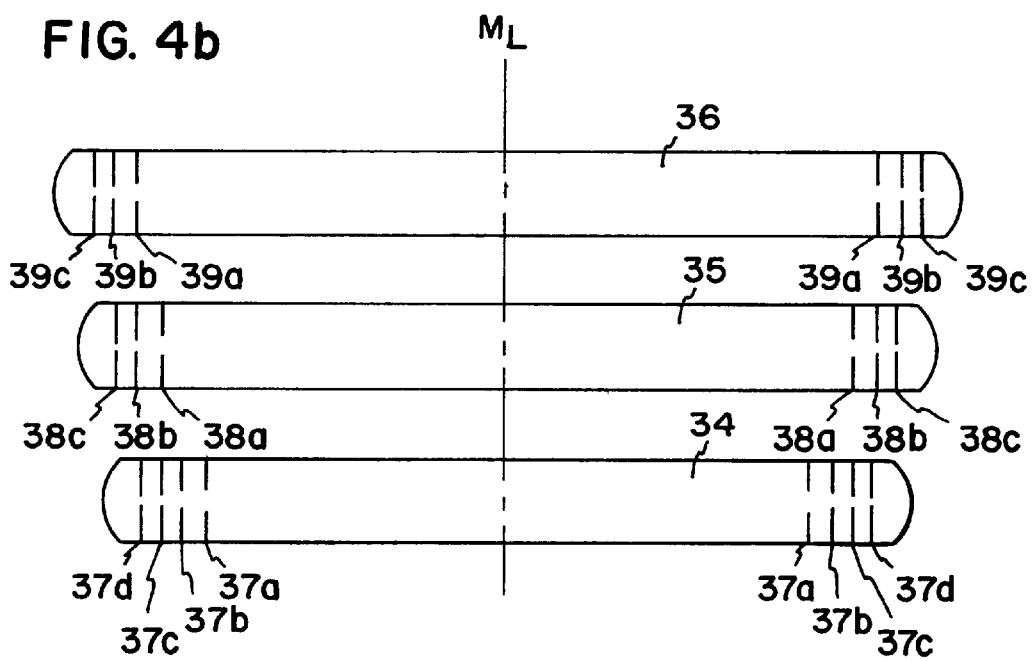

NASAL SUPPORT DEVICE FOR ANIMALS AND METHOD

FIELD OF THE INVENTION

The present invention is directed to facilitating air flow through the nasal passages of an animal. Specifically, the invention provides nasal support devices and methods for supporting soft tissue structures of the nasal passages of an animal.

BACKGROUND OF THE INVENTION

Portions of the following discussion of the nasal anatomy of domestic animals are excerpted from R. Nickel et al., *The Viscera of Domestic Mammals*, (2nd revised ed.), Springer-Verlag, New York, Hiedelberg, Berlin (1979), pp. 211–221. This is an excellent text on the comparative visceral anatomy of domestic mammals. As used herein, the terms "mammal" and "animal" are used synonymously and refer to non-human mammals.

The nasal anatomy of animals is considerably different than that of a human. Unlike the human nose that projects distinctly from the face, in many animals, the nose is incorporated into the face and forms the large dorsal and lateral areas rostral to the eyes. The nostrils at the apex of the nose are the entry to the respiratory system. Once passing through the nostrils, inspired air moves through the nasal cavities and continues into the nasopharynx, larynx, trachea and lungs.

At the apical entrance to the nose the nostrils are partitioned by the nasal septum to divide the nasal cavity into right and left halves. The caudal portion of the septum is typically bony, while rostrally the septum consists of cartilage which becomes progressively more flexible toward the apex.

The wall of the nose consists of skin externally and a middle supporting layer of bone caudally and cartilage rostrally. The nasal cavity is lined by a mucous membrane. The rostral bones forming the wall of the nose include the nasal, maxillary and incisive bones. The free borders of the nasal and incisive bone provide attachment for the cartilages which support the nostrils. The supporting bones and cartilages of the nose are associated with the nasal muscles that regulate the size of the nostrils.

The dorsal and ventral lateral nasal cartilages are formed by the widening of the rostral part of the nasal septum along its dorsal and ventral margins. In the horse, the ventral lateral nasal cartilage is small and may be absent. In many domestic animals, there is no lateral support for the soft tissue over the rostral nasal passage caudal to the nostril.

A further difference in the formation of the nasal cartilages of the horse is the presence of alar cartilages. The alar cartilages consist of a ventral cornu and a dorsal lamina and support the nostrils dorsally, medially and ventrally. The lamina of the alar cartilage and the medial accessory cartilage support the nasal diverticulum, a blind pouch in the dorsal aspect of the nostril.

The muscles of the nose and upper lip act to dilate the nostrils. This is particularly noticeable during labored breathing. In the horse, these muscles are well developed and can transform the normally semilunar nostrils to become circular.

The dorsal lateral area of the rostral nasal cavity that is caudal to the alar cartilages of the horse includes a region of unsupported soft tissue which can be drawn into the nasal cavity during inspiration of air into the nasal passages. The nasal diverticulum of the horse is a part of the soft tissue structures of the horse which can be drawn into the nasal cavity. When the soft tissue is drawn in, it can narrow the nasal cavity and reduce the area for the intake of air, thus reducing the air movement into the nasal passages and ultimately to the lungs where the oxygen is transferred in the pulmonary aveoli.

The physiological effects of reduced oxygen transfer at rest and during physical exertion in horses are documented. Some experts have theorized that exercise induced pulmonary hemorrhage (EIPH) in performance horses is caused by asphyxia due to abnormal resistance of a closed or partially closed upper airway. The upper airway being defined as the region of the respiratory tract lying between the nostrils and the windpipe at the level of the first rib. Dr. Robert Cook, "EIPH or AIPE? A Tufts University Researcher suggests that bleeding is not caused by EIPH, but by asphyxia", *The Equine Athlete*, p. 22–23 (March/April 1997).

Devices for dilating the outer wall tissue of the nasal passages in humans are known and described in, for example, U.S. Pat. Nos. 5,476,091; 5,533,503; 5,546,929; 5,549,103; 5,553,605; 5,611,333; and 5,653,224. Devices for supporting outer tissues of the nasal passages of animals must address the unique soft tissue and mechanical characteristics of an animal nose, particularly performance animals such as horses, camels and dogs. Support devices for the nasal passages of animals are known and described in U.S. Pat. No. 5,913,873 and International Patent Publication WO 98/47451. The entire disclosure of the foregoing patent and patent application are incorporated herein by reference.

SUMMARY OF THE INVENTION

The present invention provides support devices and methods for supporting the unsupported nasal tissues of an animal. In addition to providing features which enhance the function of a support device during use, the invention also provides components to facilitate the ease and accuracy of positioning a device on an animal's nose. The invention further provides features which address some of the needs which arise when using a support device during certain competitive events. It will be appreciated that some of the components or features of the herein disclosed devices may also be applicable for use with human nasal dilators.

Throughout the specification, guidance may be provided through lists of examples. In each instance, the recited list serves only as a representative group. It is not meant, however, that the list is exclusive.

In general, a support device according to the invention provides support to the right and left lateral vestibular walls of a domestic animal. The device can also include a surface layer, a support layer, and an engaging layer. The support devices included can also include a carrier layer to facilitate handling and positioning of the device on an animal's nose. In some preferred embodiments, the support device is a dark color.

In alternative embodiments, the invention provides facilitation to air flow in the nasal passages of an animal by supporting the caudal apex region of the vestibular walls of the animal.

The disclosed support devices can be used on an animal that is running free in a pasture, or wearing saddlery, harnesses or other equipment that may be attached to the nose of the animal while performing physical activity.

The devices and methods of the invention are particularly advantageous for use in horses and are beneficial for use during athletic performance or for reducing the occurrence, severity or effect(s) of respiratory diseases in an adult or young animal.

BRIEF DESCRIPTION OF THE DRAWINGS

FIG. 3 is a bottom exploded view of the nasal support device of FIG. 1;

FIG. 4b is a top view of one embodiment of lift members according to the invention.

DETAILED DESCRIPTION OF THE INVENTION

Figure 1:
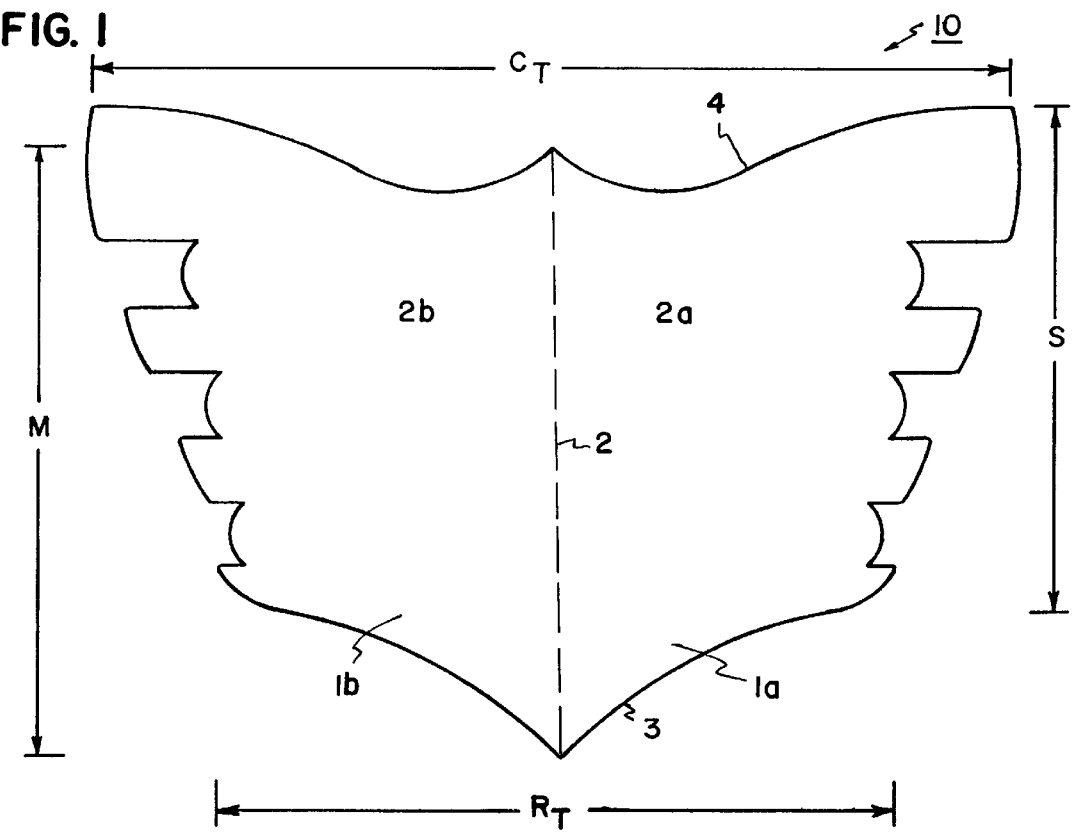
FIG. 1 is a top plan view of one embodiment of a nasal support device according to the invention.

The invention is directed to devices and methods for supporting tissues at the rostral aspect of the nasal cavity of domestic animals. Specifically, the devices and methods disclosed provide support for the unsupported region of the "vestibule" in the rostral nasal cavity. While the components and features of the disclosed devices are particularly advantageous for animal devices, some of the components and features may also be advantageously used with nasal dilators for humans.

In general, a support device of the invention can be used anytime it is desired to facilitate or enhance nasal air intake. In addition to facilitating air flow, the support devices can also be used to treat or prevent respiratory ailments in adult or young animals. The devices and methods of the invention may be particularly beneficial in horses for reducing the severity or effect(s) of respiratory conditions such as laryngeal hemiplegia, chronic obstructive pulmonary disease (COPD) or exercise related pathologies such as myositis, dorsal displacement of the soft palate (DDSP), exercise induced pulmonary hemorrhage (EIPH), etc.

As used herein, the term "rostral" refers to that aspect of the nose closest to the apex of the nose. "Caudal" refers to that aspect of the nose closest to the poll or caudal aspect of the head. The "vestibule" refers to the rostral aspect of the nasal cavity that is defined by the alar cartilages rostrally, the incisive bone ventrally, the nasal bone dorsally, the caudal intersection of the incisive and nasal bones caudally, and the nasal septum medially. The supported regions of the vestibule are generally supported by bone or cartilage.

The "unsupported" region of the vestibule is also referred to as the "lateral (free) wall" of the vestibule or "vestibular wall". The lateral wall of the vestibule includes the unsupported soft tissue defined by the nostrils rostrally, the lateral free border of the nasal bone dorsally, the dorsal free border of the incisive bone ventrally, and the intersection of the nasal and incisive bone caudally. In the horse, the dorsal border of the unsupported region can include the dorsal lateral nasal cartilage. In some species, the ventral border can include the ventral lateral nasal cartilage. For purposes herein, the vestibular wall can be divided into at least two portions, a rostral portion being that portion nearest the nostrils and a caudal portion being that portion nearest the intersection of the nasal and incisive bone. The region including about the caudal one quarter to one third of the vestibular wall is referred to as the "caudal apex region" and is more fully described below.

Herein, "soft tissue" has its general meaning including skin, muscle, fat, connective tissue or associated integumentary structures.

Some exemplary embodiments of support devices of the invention and components are described below. Throughout the specification guidance may be provided through lists of examples. In each instance, the recited list serves only as a representative group. The examples of the groups are not meant to be limiting.

In a typical embodiment, a support device provides support to at least a portion of the right and left lateral vestibular walls of an animal. Generally, a support device includes a right and left side piece, each including a support layer, which when secured to the nose of the animal are positioned to provide structural support to some or all of the right and left lateral vestibular walls. The "right" and "left" side pieces can also be referred to as "first" and "second" or "second" and "first" side pieces. In some embodiments, the support device is bilaterally symmetrical and the side pieces of the device meet at the midline in the midline region of the device. According to this embodiment, when the support device is secured to the nose of an animal, the intersection of the right and left side pieces at the midline preferably overlie the intersection of the left and right nasal bones and the right and left side pieces overlie the first and second vestibular walls, respectively.

The side pieces and the midline region of the support device each have a rostral end, a caudal end and a rostral-poll dimension. Due to the size and anatomical configuration of the surface area of the vestibular free wall of, for example, a horse, to provide sufficient support to benefit the animal, the rostral-poll dimension at the midline region of a support device is preferably substantially equal to or greater than the rostral poll dimension of the side pieces. Hence, in one embodiment, the rostral-poll dimension of the midline region is at least as great as the rostral-poll dimension of either of the side pieces. In an alternative embodiment, the rostral- poll dimension of the midline region is greater than the rostral-poll dimension of the right or left side piece.

As used herein, the term "support" refers to reducing the amount of narrowing of the nasal passage that can occur during inspiration or expiration of domestic animals. Accordingly, "support" can include some drawing in of the vestibular free wall into the rostral nasal passage during inspiration, but less than that which would occur without a device of the invention. "Support" also includes maintaining the position of the external soft tissue over the rostral nasal passage in a neutral position. As used herein, "neutral" refers to a state where the unsupported vestibular tissues are neither drawn into the nasal cavity nor protruding externally relative to a resting position. In some arrangements, "support" also includes maintaining the vestibular free wall in a "distended" outward position relative to the neutral position.

The configuration, arrangement and components of a support devices disclosed herein takes into account the anatomical and physiological characteristics of the vestibular free wall, the bony structures defining the borders of the vestibular free wall, unique problems presented in applying the device to an animal as well as equipment used on or around an animal wearing a nasal support device.

The size of a device of the invention can vary. Appropriate size devices configured for an animal typically correspond with muzzle size which can vary with the body size, breed, age, and sex, of the animal. It is foreseen that smaller size support devices for young animals, such as calves and foals can be beneficial in treating, for example, upper or lower respiratory ailments. In some embodiments, the rostral-poll midline dimension of an NSD for an average sized adult horse is about 3 to 16 cm, preferably 6–14 cm and the rostral poll dimension of the right and left side can be about 3 to 12 cm. However, larger and smaller sizes may be used.

The transverse dimension of an NSD can also vary. The "transverse dimension" is defined as the length of the device from the lateral edge of a first side of the device to the lateral edge of the second side of the device. The transverse dimension can be approximately equal at the rostral and caudal edges. Alternatively, the transverse dimension can vary in a single device depending if measured, for example, along the caudal edge, the rostral edge, or somewhere in between.

Typically, a support device according to the invention includes at least a "support layer" and an "engaging layer". A release liner which is peelably attached to the engaging layer is also typically included. In some embodiments a "surface layer" can be present to cover the side of the support layer that is away from the nose of the animal when the device is secured to the nose of the animal. Some embodiments can also include a carrier layer which can be removably attached to the surface layer to facilitate handling and proper placement of the support device on an animal's nose. The exterior color of the surface layer is preferably selected to reduce the likelihood of the device causing interference with equipment used for determining results of a particular competitive event.

The support layer of the device provides the majority of the support for the vestibular free wall of the nasal passage. Generally, the support layer comprises one or more "lift members." As used herein a "lift member" can be prepared from any suitable material which provides the desired support to the vestibular free wall. Examples of suitable materials for a lift member include thermoplastic resins, thermoset resins, shape memory metals, alloys, leather, etc. The lift member can be an open mesh or solid material. One example of a preferred material for a lift member is a biaxially oriented polyester such as MYLAR® available from DuPont Films, Wilmington Del. Other suitable materials for a lift member are disclosed in U.S. Pat. No. 5,913,873 and International Patent Publication WO 98/47451 which are incorporated herein by reference.

In some embodiments, the lift members can be a generally uniform thickness throughout their length and width. The thickness of the lift members can typically be selected based on the support needed, and is generally the same throughout. However, the lift members can also vary in thickness in different regions of the device. In addition, a lift member need not be the same width throughout its length. That is, a lift member can be wider at the ends of the lift member and narrower near the midline region. Alternatively, a lift member can be wider near the midline region and narrower at the ends.

For an adult large animal such as a horse, a suitable thickness for a lift member prepared from polyester such as MYLAR® is about 0.008 to about 0.020 inches. In one preferred embodiment, the thickness of a support member for an average size adult horse is about 0.014 inch.

The support layer can include one or more lift members. The lift members can be positioned parallel to the transverse axis of the device and extend partially or completely to the lateral edges of the device. Three to six lift members are preferred. When more than one lift member is used, the width, length and spacing of the lift members can vary based on the overall dimensions of the particular device. Also, the length of the individual lift members can vary in a single device so as to traverse some or all of the dorsal-ventral dimension of the vestibular free wall. Preferably, the transverse length dimension of a lift member is sufficient to traverse the midline of the animal's nose and extend to the right and left side pieces beyond the dorsal lateral nasal cartilages to support the right and left vestibular free walls. In some embodiments, the lift members can extend beyond the ventral edge of the vestibular free wall to a point lateral to the incisive bone.

When using multiple lift members, the spacing between individual lift members can affect the adherence and overall functioning of the device. When two or more lift members are used, the width of the lift members and the spacing between lift members are selected for the device to provide the desired support to the vestibular wall with sufficient flexibility to reduce the chance of irritation due to localized pressure at leveraging points on the animal's nose. Use of multiple lift members advantageously provides for torsional flexibility of the device which facilitates function and reduces the likelihood of disengagement of the device when subjected to the unique mobility of an animal's vestibular tissues. In one exemplary embodiment of a support device for an average size adult horse, the length of the lift members can be about 4–18 cm, preferably about 9–13 cm, the width can be about 0.2 to 2 cm and the spacing between lift members about 0.2 to 2 cm, preferably about 0.3 to 1.0 cm.

A support device according to the invention also includes an engaging layer. The engaging layer provides for securing the support device to the animal's nose, typically, by use of an adhesive. Preferably, the adhesive is biocompatible and provides minimal or no contact irritation when applied to the external tissues of an animal.

Suitable materials for the adhesive of the engaging layer are single or double coated medical tapes, transfer adhesives, liquid adhesives, pressure sensitive adhesives (PSA), etc. A release liner is preferably applied to the adhesive of the engaging layer to cover the adhesive surface until the support device is applied to an animal. As will be described below, the release liner can comprise one or more sections which can be selectively removed from the engagement layer to facilitate positioning of the support device on the nose. Examples of suitable adhesive systems include No. 1509 double sided medical tape, No. 9942 Hydrocolloid Skin Protective Adhesive and No. 1524 transfer adhesive available from 3M Co., St. Paul, Minn. One presently preferred adhesive is Dermamed DM-2009, available from Dermamed, 381 Geneva Avenue, Pallmadge, Ohio 44278.

A support device also includes a surface layer. The surface layer is visible when the device is applied to the nose of an animal. Thus, one side of the surface layer faces the soft tissue of the animal's nose and a second side faces away from the nose. The side facing the animal's nose can include an adhesive to adhere the surface layer to the support layer, to the engaging layer that may be exposed between lift members of the support layer, or to a pad layer, if used. A suitable surface material can be breathable or non-breathable. One example of a suitable surface layer is No. 9910 non-woven medical tape available from 3M Co., St. Paul, Minn.

The color of the surface layer is preferably selected so as to reduce glare which can interfere with photographs taken to determine the outcome of a performance event such as a finish line photograph taken in a horse race. Examples of suitable colors which cause reduced glare are dark colors such as black, dark blue, dark green, dark gray, dark brown, etc.

The engaging layer may extend only to the peripheral extent of the lift members of the support layer. Alternatively, the periphery of the engaging layer can extend beyond the peripheral extent of the lift members of the support layer (i.e., laterally, rostrally and caudally). In some preferred embodiments, the periphery of the engaging layer can extend beyond the support layer to provide improved engagement of the support device to the animal's nose. In one such embodiment a region of about 0.5 cm to 4 cm, preferably about 1.0–2.0 cm of engaging layer extends beyond the lateral extent of the lift members of the support layer and 1.0–3.0 cm beyond the rostral-caudal extent of the support layer. The surface layer typically extends the same distance beyond the lift members as does the engaging layer.

A support device according to the invention can also include a "carrier layer". The carrier layer can be removably adhered to the side of the surface layer away from the animal's nose. The carrier layer can be made from any suitable material including paper, metal foil, plastic, cardboard, etc. The carrier layer is preferably adhered to the surface layer using an adhesive system which provides a peel resistance which is less than the peel resistance between the adhesive of the engaging layer and the animal's nose when the support device is adhered to the animal's nose. Suitable adhesive systems for adhering the carrier layer to the surface layer are known and disclosed in, for example, U.S. Pat. Nos. 3,691,140; 4,994,322; 5,266,402; 5,502,109; and 5,719,247. The entire disclosure of each of these patents is incorporated herein by reference. One preferred adhesive is No. 9425 available from 3M Co., St. Paul, Minn. This adhesive system is a double side tape wherein a first side of the tape (applied to the carrier layer) has a greater peel resistance than the second side of the tape (applied to the surface layer) and the peel resistance of the second side of the tape is less than the peel resistance of the adhesive between the engaging layer and the animal's nose.

The perimeter edge of the carrier layer can follow the perimeter edge of the surface layer of the support device or the perimeter edge of the carrier layer can extend beyond the perimeter edge of the surface layer. Alternatively, portions of the carrier layer can extend beyond the perimeter edge of the surface layer and other portions follow the perimeter edge or not extend to the perimeter edge of the surface layer. Extending the perimeter edge of the carrier layer beyond the perimeter edge of the surface layer provides a region of the carrier layer which can be grasped for handling or removing the carrier layer from the surface layer without contacting the adhesive of the engaging layer. Alternatively, the carrier layer can be slit to provide an internal edge to grasp for removing the carrier layer from the surface layer. In a preferred embodiment, the perimeter edge of the carrier layer can be configured to provide a guide for positioning of the support device on an animal's nose.

Thus, after removal of some or all of the release liner from the adhesive of the engaging layer, the carrier layer can be grasped during application of the device without contacting the adhesive of the engaging layer. Once engaged to the nose, the carrier layer can be peelably removed from the support device. The carrier layer can also be marked with instructions for proper positioning and orientation of the support device to assist the person applying the device to the animal.

In another embodiment of the invention, a support device can comprise two separate pieces, one for supporting a portion of each of the right and left vestibular wall For example, only the caudal aspect of each of the vestibular walls may be supported by the device. According to one such embodiment, the support device can extend from the nasal bone to the incisive bone, across the "caudal apex region" of the vestibular wall near the intersection of the nasal and incisive bones. In an alternative embodiment, the support device can extend rostrally over the caudal apex of the vestibular wall from a location caudal to the intersection of the incisive and nasal bones. In another embodiment, the support device can extend from the nasal bone to the incisive bone, across the caudal apex of the vestibular wall, and extend caudally over the intersection of the incisive and nasal bones.

Examples of support devices and methods of the invention will now be further described by reference to the following illustrated embodiments.

DETAILED DESCRIPTION OF THE ILLUSTRATED EMBODIMENTS

Anatomical reference points and embodiments of a nasal support device according to the invention will be described with reference to the drawings, using the horse as an exemplary animal, wherein like reference numerals represent like components and assemblies throughout the several views. Reference to the drawings is not intended to limit the scope of the invention to the illustrated embodiments.

FIG. 1 is a top plan view of the configuration of one embodiment of a nasal support device (NSD) 10 according to the invention. Dimensions which can be used to characterize an NSD are shown wherein letters followed by a subscript "T" are transverse dimensions. Thus, $C_T$ is the caudal transverse dimension, $R_T$ is the rostral transverse dimension, S is the rostral-poll dimension of the side piece and M is the rostral-poll dimension at the midline of the device. The bottom plan view of NSD 10 is substantially identical to the top plan view of FIG. 1 except that the support layer, shown in FIGS. 3 and 4, may be visible.

The NSD 10 includes a first side piece 1a and a second side piece 1b that intersect at the midline 2 of the midline region 2a and 2b. In use, the rostral end 3 is oriented towards the apex of the animal's nose and the caudal end 4 is oriented towards the eyes of the animal. In the embodiment of FIG. 1, the midline rostral-poll dimension M is at least equal to the rostral-poll dimension S of side pieces 1a and 1b. In preferred embodiments, the rostral-poll dimension of the NSD at the midline 2 is greater than the rostral-poll dimension S of the first or second side pieces 1a, 1b. It will also be appreciated that in the illustrated embodiment, the rostral transverse dimension $R_T$ is less than the caudal transverse dimension.

Bony anatomical structures which surround the vestibular free wall which is supported by a support device of the invention are described with reference to FIG. 2 which is a profile view of the bony anatomy of the rostral region of the horse's head. A more complete discussion of the relevant anatomy is disclosed in U.S. Pat. No. 5,913,873, the entire disclosure having previously been incorporated herein by reference. Briefly, the lateral free wall of the vestibule is defined dorsally by the lateral aspect of the nasal bone 5, ventrally by the incisive bone 6, and caudally by intersection 7 of the nasal 5 and incisive 6 bones. The rostral aspect of the vestibular free wall is bordered by the nostril (not shown).

Figure 2:
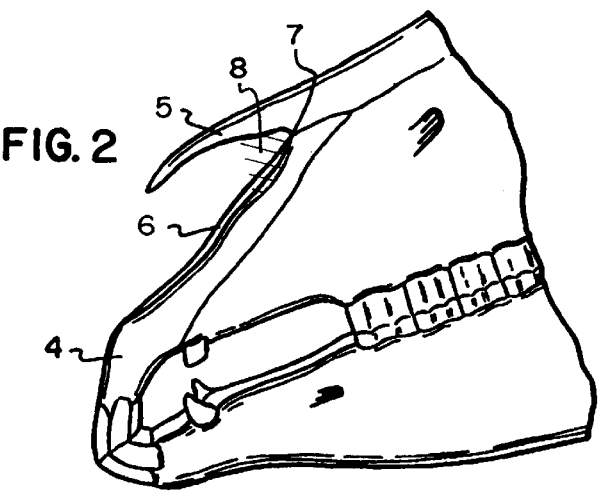
FIG. 2 is a profile view of the bony anatomy of the rostral nasal cavity of the horse.

The shaded area 8 in FIG. 2 depicts the approximate area underlying the "caudal apex region" of the vestibular wall. In some embodiments, a support device of the invention may be configured to support only the caudal apex region of the vestibular wall to facilitate air flow through the nasal passages. The caudal apex region is nearest the nasal valve region of the nasal passages which is particularly vulnerable to narrowing under certain conditions.

Figure 4A:
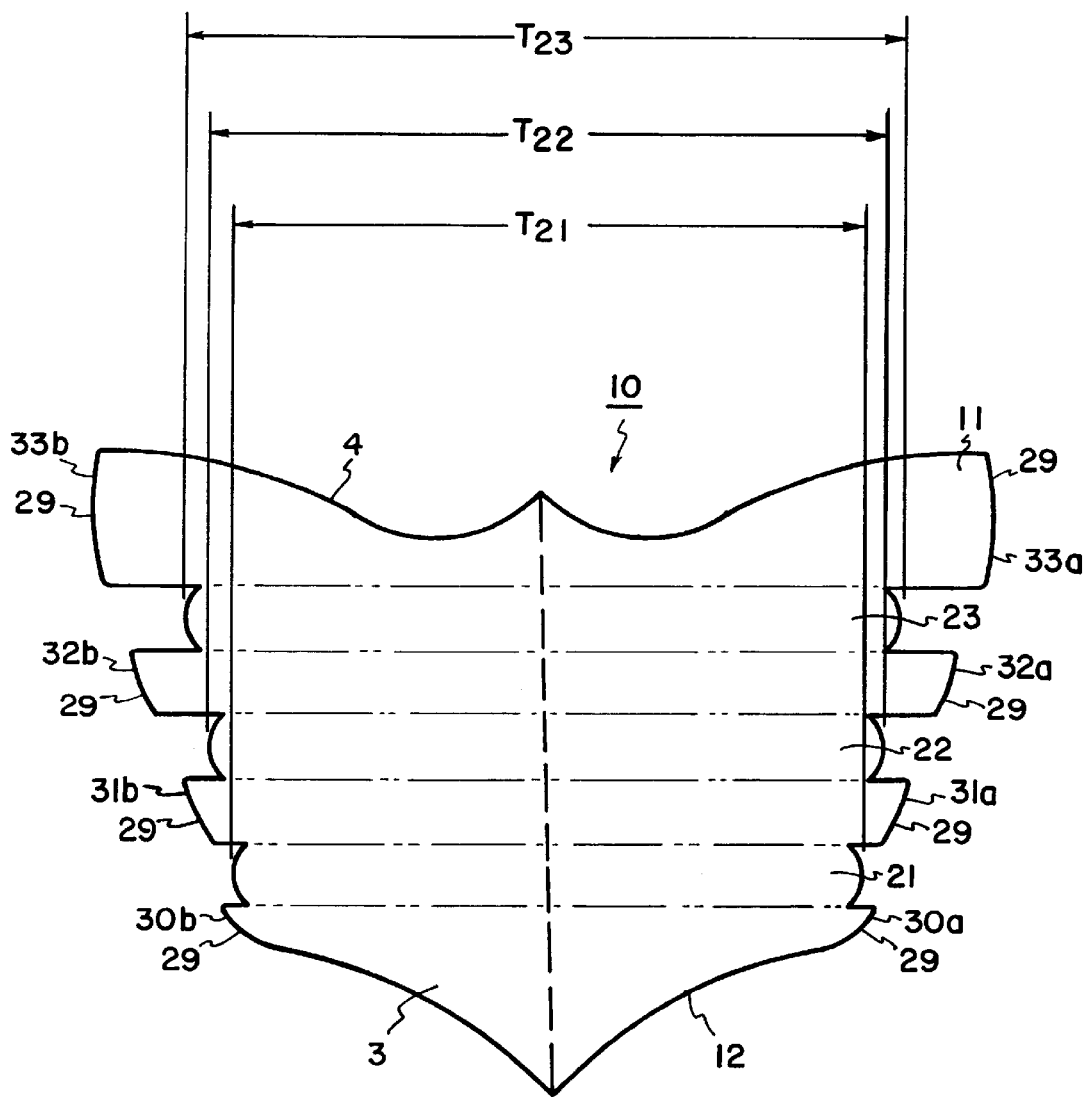
FIG. 4a is a top view of the nasal support device of FIG. 1 with the support layer illustrated in phantom.

FIG. 3 is a bottom exploded view of NSD 10 illustrating a surface layer 11, support layer 12, engaging layer 13 and release liner 14. A carrier layer is not shown in this view. FIG. 4a is a top plan view of the NSD 10 of FIGS. 1 and 3 showing rostral 21, intermediate 22 and caudal 23 lift members in phantom lines. In this embodiment, the transverse length $T_{23}$, $T_{22}$, and $T_{23}$ of lift members 21, 22, and 23, respectively, increases from the rostral end 3 to the caudal end 4 of NSD 10. In addition, lateral engagement extensions 29, comprise rostral (30a, 30b), rostral/intermediate (31a, 31b), caudal/intermediate (32a, 32b) and caudal (33a, 33b) lateral engagement extensions. Lateral engagement extensions 29 are comprised of surface layer 11 and engagement layer 12 which extend beyond the transverse length (i.e., lateral extent) of lift members 21, 22, and 23 to facilitate engagement of NSD 10 to the nose of the animal. The functional aspects of the lateral engagement extensions can be embodied in various overall device appearances.

FIG. 4b is a top view of an alternative embodiment of the lift members of NSD 10. In this view, only lift members 34, 35, 36 are shown and they are in the same relative position as shown in phantom lines in FIG. 4a. At the lateral extent of each of lift members 34, 35, 36, there are pairs of notches 37a–d, 38a–c, 39a–c which can penetrate through a partial or full thickness of each of the lift members 34, 35, 36. In the illustrated embodiment, four pairs of notches 37a–d are present at the lateral end of rostral lift member 34 and three pairs 38a–c, 39a–c are present at the lateral end of intermediate lift member 35 and caudal lift member 36. It will be appreciated that in this embodiment, the most lateral notches 37d, 38c, 39c of each lift member traverse a greater portion of the width of the lift members (i.e., smaller unnotched region between notches of a pair) than do notches nearer to midline ML of lift members 34, 35, 36. The number of notch pairs can be varied. Typically, if additional notch pairs are added, they are added nearer the midline $M_L$ region of the lift member.

The effect of notches which traverse an increasing portion of the width dimension of the lift member from nearest the midline $M_L$ to the lateral end is to gradually decrease the peel force exerted on the engaging layer between the support device and the animal's nose and convert it to a shear force to facilitate engagement of the NSD 10 to the animal's nose.

Referring to FIG. 3, release liner 14 can comprise a single section or have a single or multiple slits to make a multiple section release liner. Suitable release liners for use with an adhesive of the engagement layer are known. In one preferred embodiment, illustrated in FIG. 3, release liner 14 comprises three components, a first lateral piece 40, a second lateral piece 41 and an intermediate piece 42. According to this embodiment, when applying NSD 10 to an animal's nose, intermediate piece 42 can be removed first and NSD 10 positioned over the nasal bones 5, and the midline region 44c of adhesive 44 of engagement layer 13 lightly engaged to the skin over the nasal bones. Some repositioning can be performed before the lateral aspects 44a and 44b of the adhesive 44 is exposed. Once the proper final position of the NSD 10 is determined, first lateral piece 40 and second lateral piece 41 of release liner 14 can be removed and the lateral aspects 44a and 44b of adhesive 44 secured to the animal's nose.

In the embodiment of FIG. 3, the bottom side 50 of surface layer 11 (i.e., the side towards the animal's nose when in use) includes an adhesive layer 51 to adhere the surface layer 11 to the top side 52 of lift members (21, 22, 23) and to the top side 54 of engaging layer 13. The bottom side 53 of lift members (21, 22, 23) can include an adhesive 56 to adhere the lift members (21, 22, 23) to the top side 54 of the engaging layer. The bottom side 55 of engaging layer 13 includes adhesive 44 to adhere the device to the animal's nose. Each of the adhesives of NSD 10 can be a coated medical tape, transfer adhesive, liquid adhesive, PSA, etc. In one preferred embodiment, the surface layer 11 is 9910 black non-woven medical tape available from 3M Co., St. Paul, Minn., the lift members 21, 22, 23 are MYLAR® available from DuPont Films, Wilmington, Del., the engaging layer 13 is DM-2009, available from Dermamed, Pallmadge, Ohio 44278 and the release liner is DM-2009 release liner, also available from Dermamed.

Figure 5:
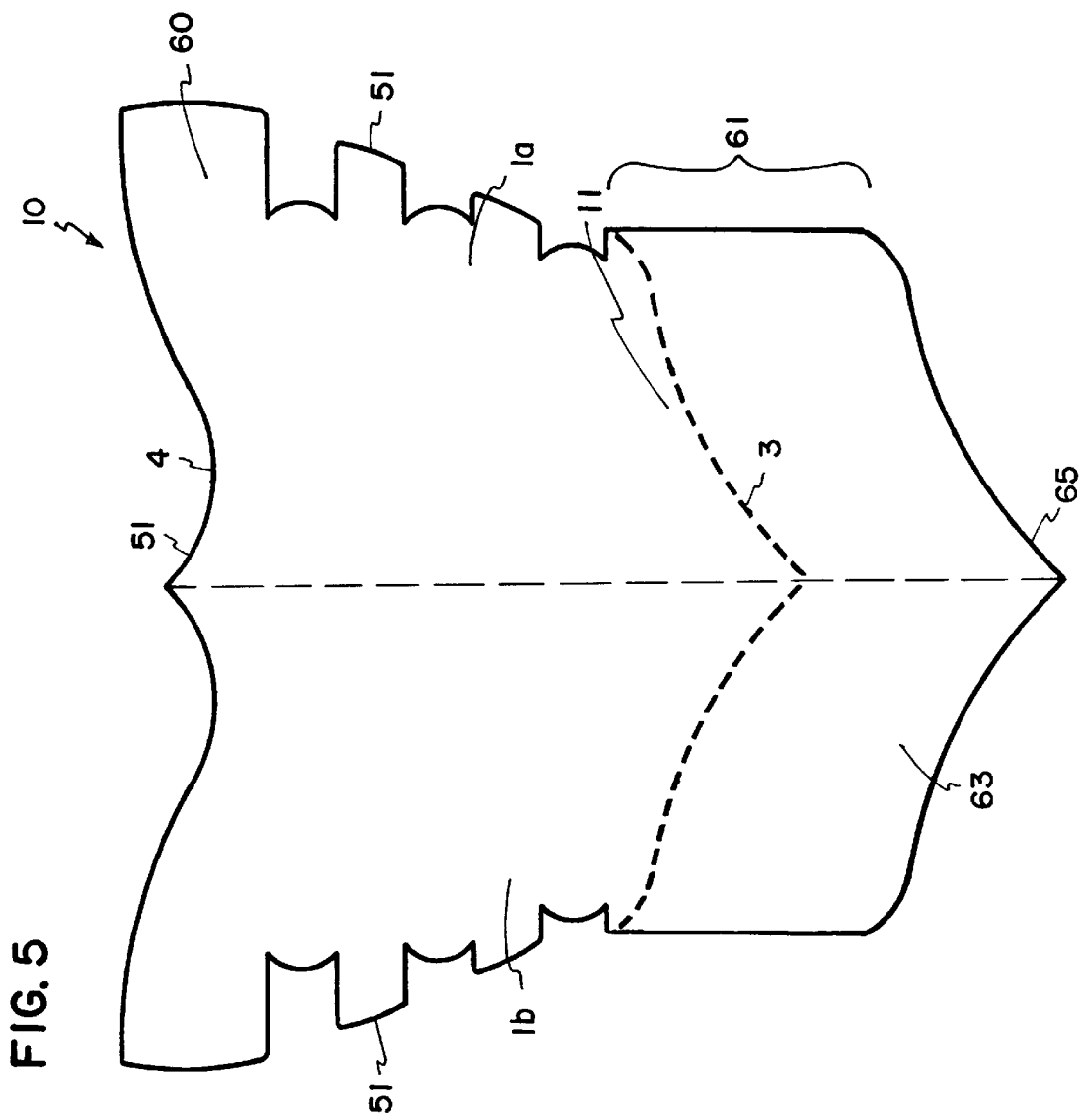
FIG. 5 is a top plan view of the nasal support device of FIG. 1 having a carrier layer.
Figure 6:
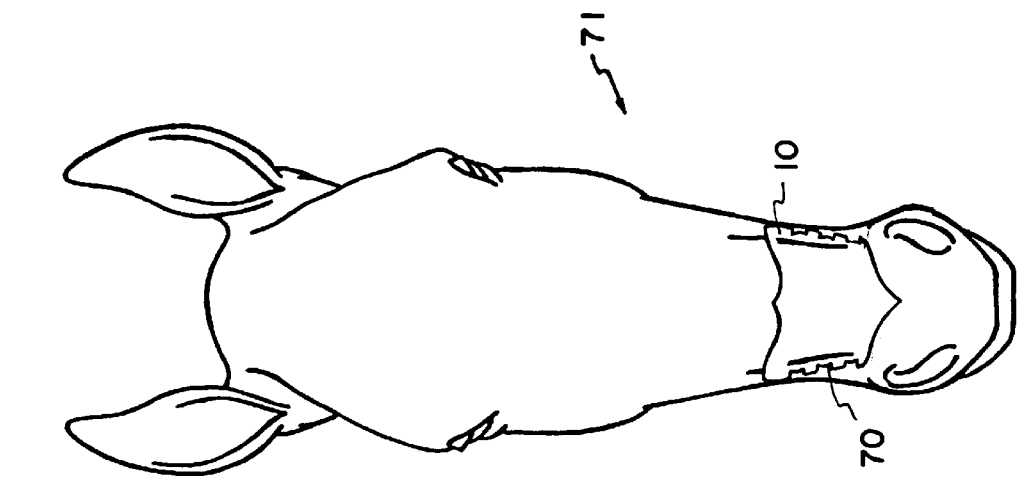
FIG. 6 is a front view of a horse having the embodiment of a nasal support device of FIG. 1 secured to its nose.

In some embodiments, an NSD can include a carrier layer. FIG. 5, is a top view of an NSD 10 including a carrier layer 60 which is releasably adhered to the surface layer 11. In this embodiment, carrier layer 60 follows the perimeter edge 51 of surface layer 11 except at the rostral end 3 of the NSD 10. At the rostral end 3, the carrier layer 60 includes a rostral extension 61. Rostral extension 61 provides a grasping portion 63, for handling NSD 10 with reduced likelihood of contacting the adhesive 44 of engagement layer 13, if the release liner has been removed. In addition, in the embodiment of a carrier layer 60 of FIG. 5, the rostral extension 61 is configured to provide an alignment guide for proper positioning of the NSD 10 on an animal's nose. Specifically, by aligning the rostral edge 65 of carrier layer 60 at the apex of a horse's nostrils, the side pieces 1a and 1b will be properly aligned over the lateral vestibular walls. FIG. 6 is a front view of an NSD 10 secured to the nose 70 of a horse 71.

Figure 7:
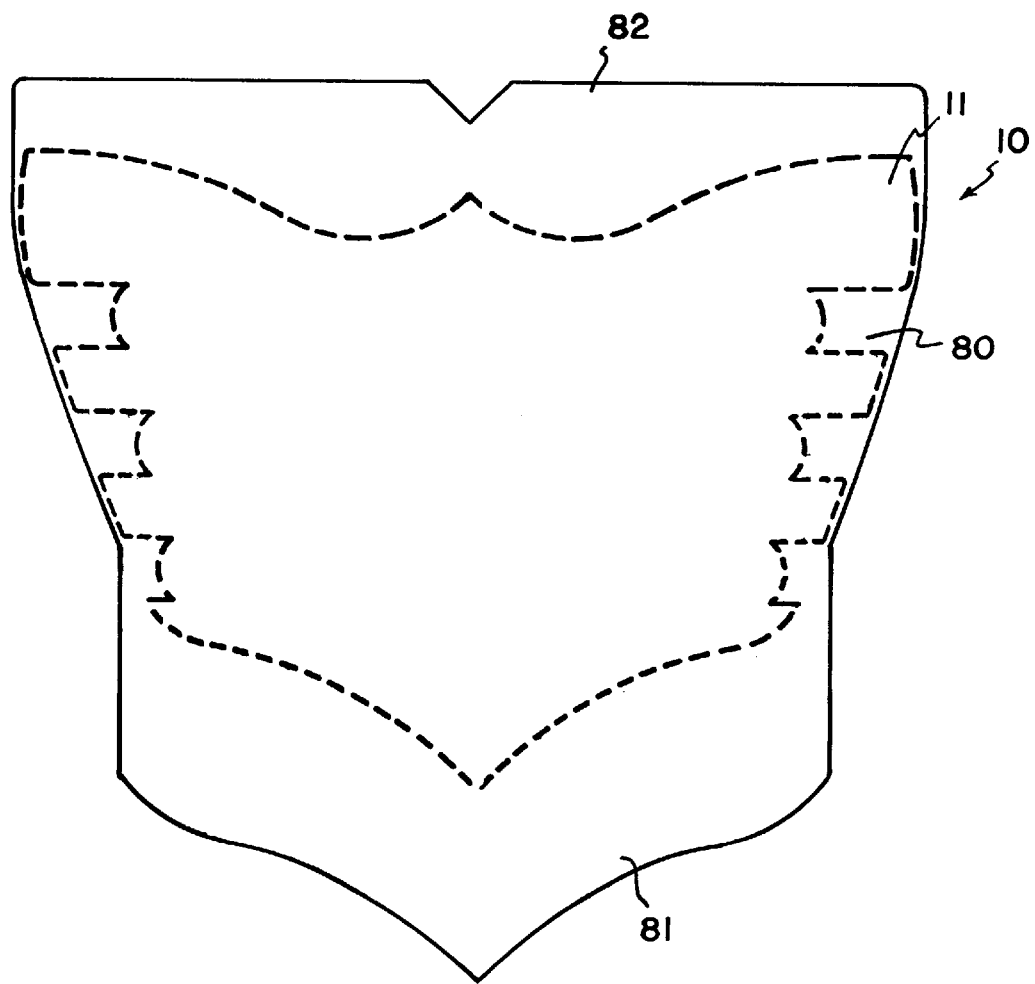
FIG. 7 is a top plan view of the nasal support device of FIG. 1 having an alternative embodiment of a carrier layer.

FIG. 7 is an NSD 10 having an alternative embodiment of a carrier layer 80 releasably adhered to the surface layer 11. As with carrier layer 60 of FIG. 5, carrier layer 80 includes a rostral extension 81. In addition, carrier layer 80 also includes a caudal extension 82 to facilitate handling and positioning of the device 10. In other embodiments, the carrier layer could be configured to provide lateral extensions or a perimeter extension around the entire device.

A carrier layer and release liner as disclosed herein can also be used with human nasal support dilators as well as with animal nasal support devices as disclosed in, for example, U.S. Pat. No. 5,913,873 and applications U.S. Ser. Nos. 09/018,603 and 09/264,464, the entire disclosures of which are being incorporated herein by reference.

Figure 8:
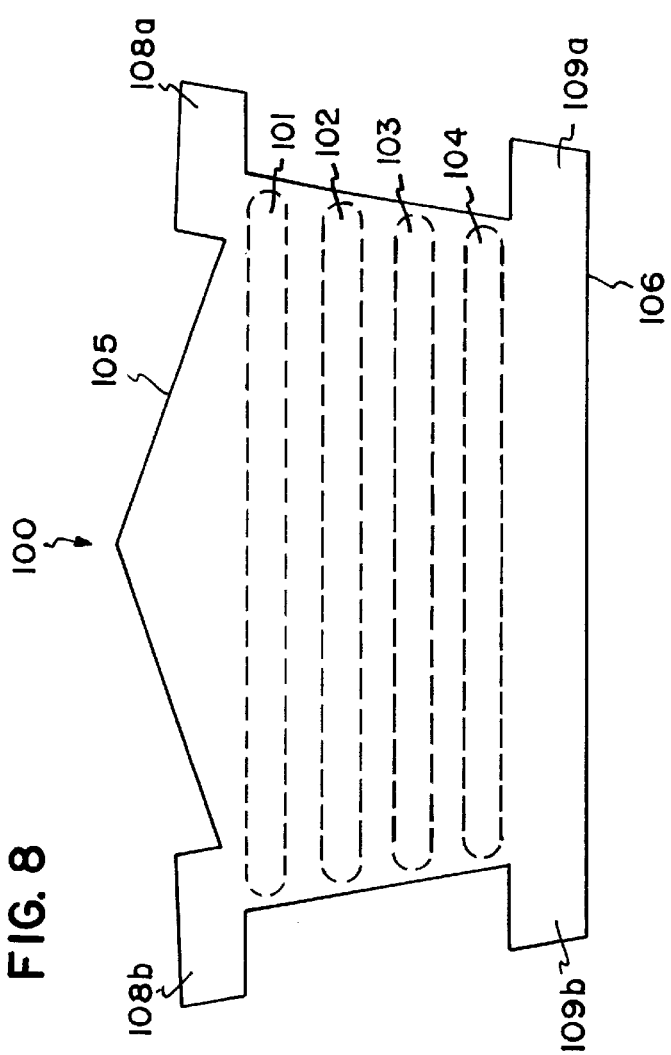
FIG. 8 is a top plan view of an alternative embodiment of a nasal support device according to the invention.

FIG. 8 is a top view of an alternative embodiment of an NSD 100 according to the invention. Four lift members 101, 102, 103 and 104 are illustrated in phantom lines. It will be appreciated that in this embodiment, lift member 101 at the rostral end 105 of NSD 100 has the longest transverse dimension and lift member 104 at the caudal end 106 has the shortest transverse dimension. Lateral engagement extensions 108a, 108b and 109a, 109b are also present for purposes previously discussed.

Figure 9:
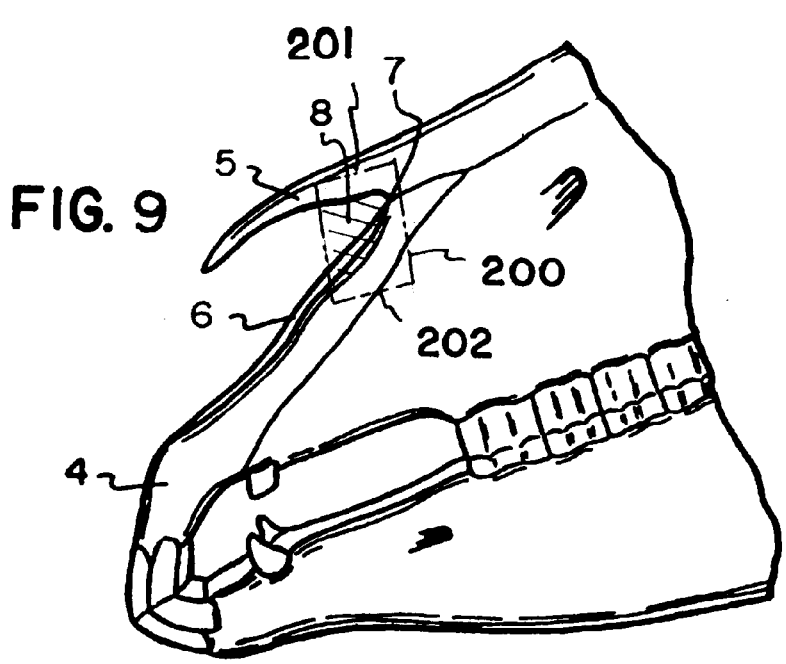
FIG. 9 is a diagrammatic representation of an alternative embodiment of a nasal support device according to the invention.
Figure 10:
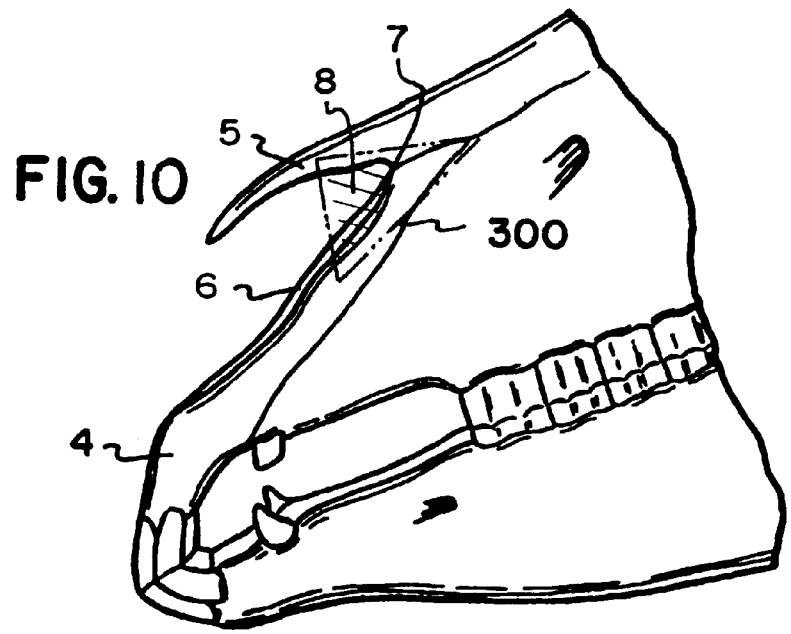
FIG. 10 is a diagrammatic representation of another alternative embodiment of a nasal support device according to the invention.

FIGS. 9 and 10, illustrate an alternative embodiment of a support device and method of the invention. For exemplary purposes, the following description will be made with illustrations of a support device applied to the skeletal anatomy of a horse to appreciate the relative positions of the anatomy and the support provided.

The embodiments of FIGS. 9 and 10 provide localized support to the caudal apex region of the vestibular wall. FIG. 9 illustrates the positioning, relative to shaded area 8, of a support device 200 when applied to the caudal apex region of the vestibular wall. As illustrated, support device 200 has a dorsal edge 201 which overlies a portion of nasal bone 5 and a ventral edge 202 which overlies a portion of incisive bone 6. The amount of dorsal edge 201 and ventral edge 202 which overlies nasal bone 5 and incisive bone 6 is preferably at least about 0.5 cm and typically about 1.0 to 3.0 cm.

FIG. 10 illustrates an alternative embodiment for supporting the caudal apex region of the vestibular wall. In this embodiment, support device 300 extends caudally beyond the intersection 7 of nasal bone 5 and incisive bone 6. Preferably, support device 300 extends about 0.5 cm to about 5.0 cm caudal to intersection 7. Support device 300 also extends dorsally and ventrally over nasal bone 5 and incisive bone 6, respectively, as described for support device 200.

It will be appreciated that although support device 200 is illustrated as a rectangle and support device 300 as a triangle, other shapes, including squares, circles, ovals, octagons, etc., can be used to provide function according to this aspect of the invention. In addition, support devices 200 and 300 can include a carrier layer, surface layer, support layer, engaging layer and release liners as described for other embodiments of the invention. The support layer can comprise one or more lift members made of previously described materials.

Thus, a support device as disclosed herein provides support for the nasal passages of an animal, particularly unsupported soft tissues. The devices can provide reduced resistance to air flow, including reduced turbulence, at rest and during exercise. In addition, the support devices can be used to treat or prevent respiratory ailments in adult or young animals.

Support of unsupported nasal tissues is particularly advantageous for animals such as horses because horses are obligate nose breathers. In preferred embodiments, a herein disclosed NSD may reduce the amount of bleeding which is associated with exercise-induced pulmonary hemorrhage (EIPH) in horses. Methods are known for determining the amount of pulmonary bleeding which occurs during EIPH. One such method includes performing pulmonary lavage post exertion and quantifying the number of red blood cells per microliter (i.e., RBC/$\mu$l) in the lavage fluid. In some embodiments, when a herein disclosed support device is worn during physical exertion by a horse susceptible to EIPH, pulmonary red blood cell counts can be reduced by at least 5%, preferably by at least 10–20%, in some embodiments by 30–40% and in some embodiments by at least 50–70% as compared to when the same horse is exercised without the NSD.

Without being limited to a particular theory, the inventors believe that support of the lateral vestibular wall, or portions thereof, over the nasal region of an animal decreases resistance to air flow and increases breathing efficiency. That is, when wearing an NSD, less energy is consumed by the animal during inspiration or expiration of air into the lungs. Resistance to air inflow/outflow is reduced by providing a cross sectional area of the nasal passages which is greater than the cross sectional area when the support device is not used. It is believed that a decrease in cross sectional area of the nasal passages requires an increase in intrapleural pressure (i.e., negative pressure) during inspiration to draw the same amount of air into the lungs. Airway resistance (R) is related to the pressure (P) across the nasal airway passage and flow (F) of air through the nasal passage by the equation: R=P/F.

The inventors believe that a high intrapleural negative pressure across pulmonary aveoli combined with high pulmonary blood pressure during exercise can cause rupture of pulmonary blood vessels which manifests as EIPH.

In some embodiments, when a herein disclosed support device is worn during exercise by a horse, nasal passage resistance can be reduced by at least about 5–10%, typically 20–30%, and in some animals, by greater than 40%. In addition, by reducing nasal passage resistance, less work is required during breathing resulting in reduced oxygen consumption and reduced $CO_2$ production for the same amount of exertion. Heart rate may also be reduced in a horse using an NSD when compared to the same horse performing at the same level of exertion without an NSD.

Having now described the invention, it will be apparent to one of skill in the art that changes and modifications can be made to the invention without departing from the spirit or scope of the appended claims. All modifications and equivalents of the disclosed invention are intended to be included within the scope of the claims.

What is claimed is:

1. A support device for supporting tissues overlying a first and second nasal passage, the support device comprising:
   an engaging layer including an adhesive for engaging the support device to the tissues;
   a surface layer;
   a support layer positioned between the engaging layer and surface layer; and
   a carrier layer releasably mounted to the surface layer.

2. The support device according to claim 1 further comprising a release liner releasably attached to the adhesive of the engaging layer.

3. The support device according to claim 2 wherein the release liner comprises a first lateral piece, a second lateral piece, and an intermediate piece.

4. The support device according to claim 1 configured to include:
   a transverse axis having a transverse dimension;
   a center longitudinal axis having a center longitudinal dimension, the center longitudinal axis being orthogonal to the transverse axis and the center longitudinal axis bisects the transverse axis;
   a first and second lateral longitudinal dimension on opposing sides of the center longitudinal dimension;
   the center longitudinal dimension greater than the first and second lateral longitudinal dimensions;
   the surface layer on opposing sides of the transverse axis being mirror images of one another.

5. A support device according to claim 4 wherein the surface layer on opposing sides of the longitudinal axis are mirror images of one another.

6. A support device according to claim 4 wherein the support device is bilaterally symmetrical across both of the transverse and longitudinal axes.

7. A support device according to claim 1 wherein the support layer includes at least two lift members.

8. A support device according to claim 1 wherein the support layer includes at least three lift members.

9. A support device according to claim 8 having an engagement extension extending laterally beyond the lift members.

10. A support device according to claim 1 wherein the surface layer is a dark color.

11. A support device according to claim 1 wherein the carrier layer includes a rostral extension.

12. A support device according to claim 11 wherein the rostral extension is an alignment guide.

13. A support device for supporting tissues overlying a first and second nasal passage, the support device comprising:

an engaging layer including an adhesive for attaching the support device to the tissues;

a surface layer;

a support layer positioned between the engaging layer and surface layer;

the surface layer is a dark color; and a carrier layer releasably mounted to the surface layer.

* * * * *

UNITED STATES PATENT AND TRADEMARK OFFICE
CERTIFICATE OF CORRECTION

PATENT NO. : 6,352,548 B1
DATED : March 5, 2002
INVENTOR(S) : Blach et al.

It is certified that error appears in the above-identified patent and that said Letters Patent is hereby corrected as shown below:

<u>Title page,</u>
Item [57], ABSTRACT,
Line 2, "animals." should read -- animals are disclosed. --

<u>Column 9,</u>
Line 22, "length $T_{23}$," should read -- length $T_{21}$, --
Line 49, "ML" should read -- $M_L$ --

Signed and Sealed this

Second Day of March, 2004

JON W. DUDAS
*Acting Director of the United States Patent and Trademark Office*